United States Patent [19]
Campbell-Smith

[11] Patent Number: 6,128,531
[45] Date of Patent: Oct. 3, 2000

[54] DELIVERY OF ICD SHOCK CAPACITOR ENERGY VIA A CONTROLLED CURRENT SOURCE

[75] Inventor: Alexander J. Campbell-Smith, Sydney, Australia

[73] Assignee: Pacesetter, Inc., Sylmar, Calif.

[21] Appl. No.: 09/053,355

[22] Filed: Apr. 1, 1998

[51] Int. Cl.⁷ .................................................. A61N 1/39
[52] U.S. Cl. ...................................... 607/7; 607/5
[58] Field of Search .............................. 607/5, 7

[56] References Cited

U.S. PATENT DOCUMENTS

| | | |
|---|---|---|
| 5,058,583 | 10/1991 | Geddes et al. .......................... 607/6 |
| 5,184,614 | 2/1993 | Collins et al. .......................... 607/4 |
| 5,350,403 | 9/1994 | Stroetmann et al. ................... 607/5 |
| 5,447,518 | 9/1995 | Pless . |
| 5,626,624 | 5/1997 | Schaldach et al. ..................... 607/24 |
| 5,725,560 | 3/1998 | Brink .......................................... 607/5 |
| 5,733,309 | 3/1998 | Kroll et al. . |
| 5,776,166 | 7/1998 | Gliner et al. . |
| 5,974,339 | 10/1999 | Baker, Jr. et al. ....................... 607/7 |

*Primary Examiner*—William E. Kamm
*Assistant Examiner*—Carl H. Layno
*Attorney, Agent, or Firm*—Gottlieb Rackman & Reisman PC

[57] ABSTRACT

An implantable cardiac device is described in which therapeutic pulses for application to a patient's heart are generated by a controllable current source. Thus, the amplitude, duration and/or other characteristics of the pulses can be readily selected. The device can be used to apply brachy- or-tachy-pacing pulses, cardioversion pulses or even defibrillation shocks.

11 Claims, 3 Drawing Sheets

6,128,531

DELIVERY OF ICD SHOCK CAPACITOR ENERGY VIA A CONTROLLED CURRENT SOURCE

BACKGROUND OF THE INVENTION a. Field of Invention

This invention pertains to an implantable cardioversion device having circuitry for shaping and controlling precisely the therapeutic pulses delivered to a patient. Alternatively, the device may be used to induce tachycardia or fibrillation.

b. Description of the Prior Art

In the present invention the term implantable cardioversion device or ICD is used to generically cover all implantable devices capable of delivering therapeutic pulses or shocks. That is, the term is intended to cover not only devices arranged and constructed to deliver cardioversion pulses, defibrillation shocks or other similar antitachycardia therapy but pacing pulses on demand for bradycardia therapy.

ICDs presently available on the marked deliver either pulses of defined duration and magnitude having relatively small energy content (in the order of 50 Microjoules) or high voltage energy content of up to 40 Joules. In either case, the energy for these pulses or shocks is derived from one or more capacitors. These capacitors are first charged to a nominal voltage, and when pulses are required, they are switched to the delivering electrodes and are discharged through the body tissues. While the defibrillation pulses are applied the capacitors cannot be charged back to their nominal value.

A further disadvantage of the present devices is that once the capacitors are switched to the electrodes, the currents generated are strictly depending on the impedance of the body and any parasitic resistivity of the electrodes. The magnitude of these currents is not otherwise limited or controlled.

OBJECTIVES AND SUMMARY OF THE INVENTION

In view of the above disadvantages of the prior art, it is an objective of the present invention to provide an ICD which is capable of delivering shocks or other types of therapeutic pulses at a predetermined controlled current magnitude.

Yet another object is to provide an ICD constructed and arranged to provide cardioversion pulses.

Other objectives and advantages of the invention shall become apparent from the following description.

Briefly, an ICD constructed in accordance with this invention includes a sensor for sensing cardiac activity in a patient's heart, a signal generator generating control signals, a power supply, and a controllable current source receiving power from the power supply, and delivery current pulses through electrodes to the patient's heart. The controllable current source is activated and controlled by the commands whereby both the timing and the shape of the current pulses is precisely selected. In one specific embodiment a controlled current source configuration is used for generating the current pulses. In a second embodiment, a controlled voltage source configuration is used.

DETAILED DESCRIPTION OF THE INVENTION

Figure 1:
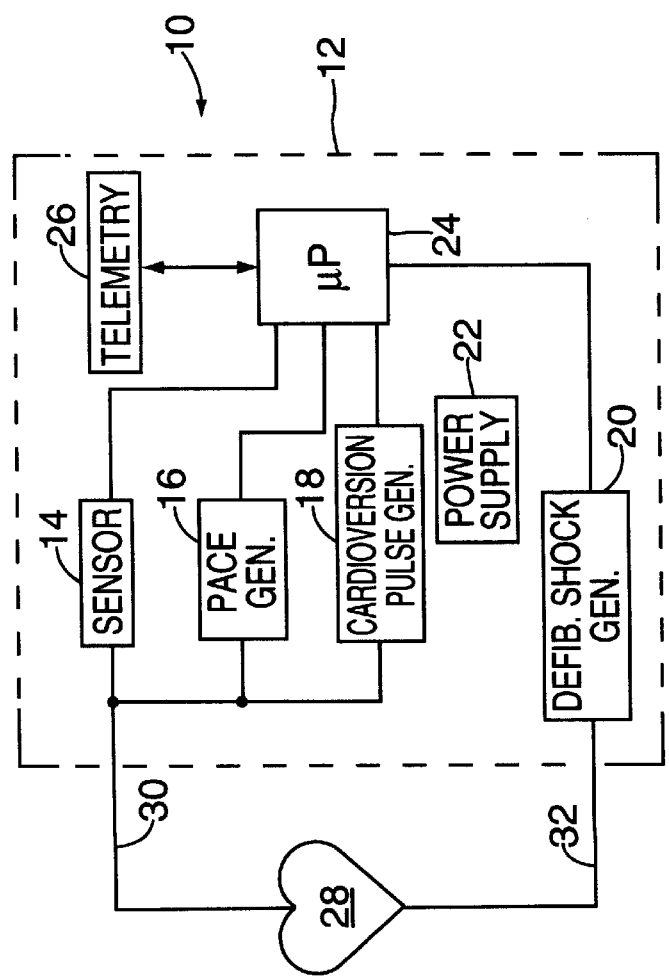
FIG. 1 shows a block diagram of an ICD constructed in accordance with this invention.

As shown in FIG. 1, typically an ICD 10 consists of a housing or case 12 which holds the various electrical circuitry such as a sensor 14, a pacing pulse generator 16, a cardioversion pulse generator 18 and a defibrillation shock generator 20. Power for the generators and the other circuitry is derived from a power supply 22. A microprocessor 24 is used to control the various circuits as described in more detail below. Communication to the outside world takes place through a telemetry circuit 26.

The housing 12 may be used as an electrode or it may be electrically isolated. Pulses from generator 16 or 18 are sent to the heart 28 via lead 30 and intrinsic cardia signals are sensed by sensor 14. In addition, in many instances, current delivered by the electrodes may also flow from the heart through the intermediate tissues to the housing 12.

Figure 2:
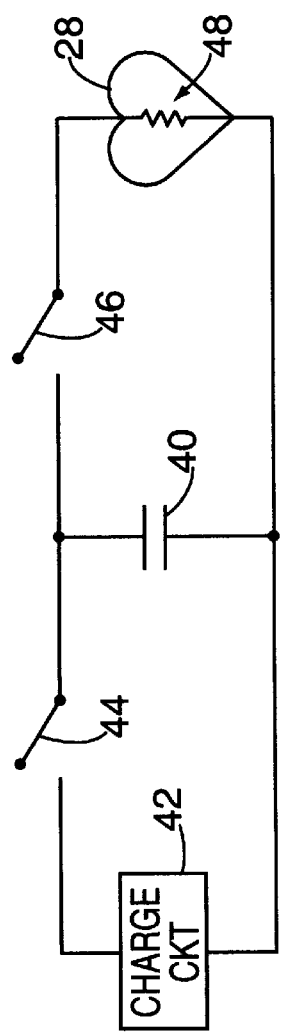
FIG. 2 shows a simplified elementary diagram for a prior art charging and discharging circuit.

As shown in FIG. 2, prior to the present invention, a pulse was generated by cardioversion pulse generator 18 or defibrillator shock generator 20 as follows. First, a capacitor 40 was charged by a charging circuit 42 by closing a switch 44. (In FIG. 2, capacitor 40 may represent a plurality of capacitors hooked in parallel). It should be understood that this process may involve using a resonant tank circuit, especially if the required voltage V on capacitor 40 was relatively high, i.e. in the order of 700-vc. Next, switch 44 was opened and switch 46 was closed. Switch 46 connected the capacitor 40 to the leads and electrodes leading to the heart 28. Closing switch 46 allowed the capacitor 40 to discharge through the heart 28, schematically represented herein by resistance 48. If required, a plurality of switches arranged in a bridge could be used to provide a multiphase pulse to heart 28. However, the current through the heart had an initial peak value V/R where V was the voltage of capacitor 40 and R was the impedance of resistor 48, and decayed exponentially in a manner characteristic of RC circuits.

Figure 3:
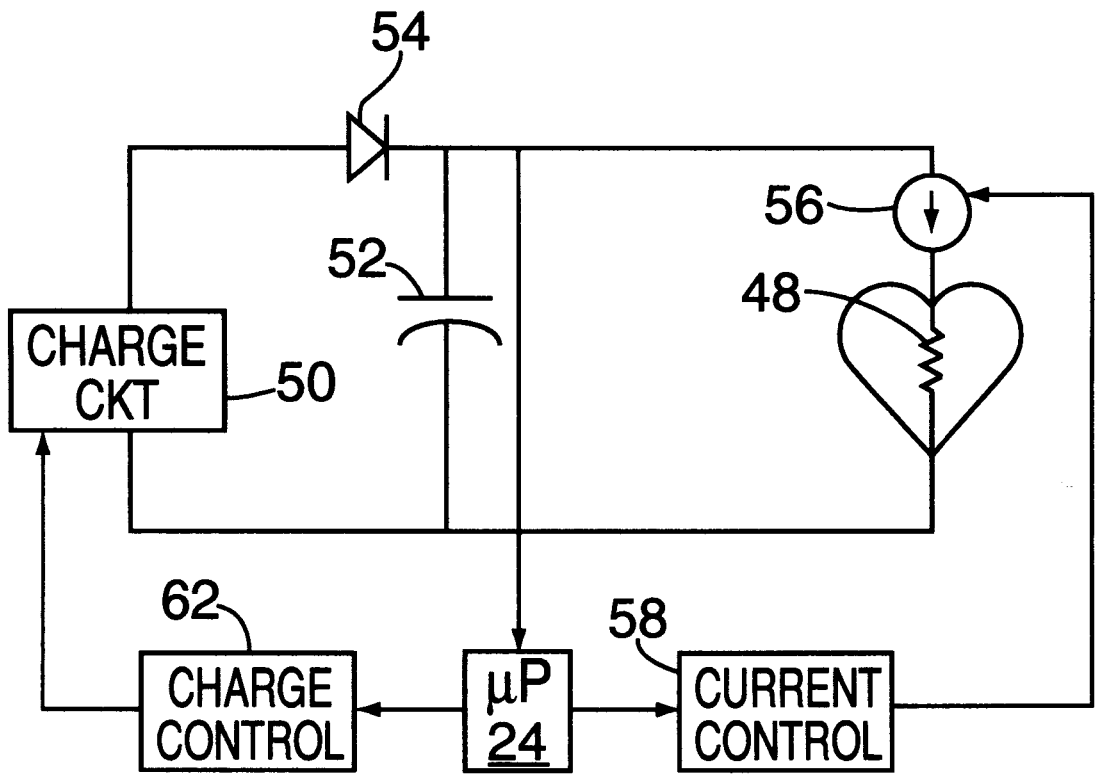
FIG. 3 shows a simplified elementary diagram of a discharge circuit in accordance with the present invention.

FIG. 3 shows how one or more current pulses are applied in accordance with this invention. In this FIG., charge circuit 50 charges a capacitor 52 through a diode 54. The capacitor 52 is discharged through a current source 56. Importantly, the voltage across the current source 56 is monitored by the microprocessor 24. Additionally, the circuit is also provided with a current control circuit 58, and a charge control circuit 62, all of these circuits operating under the control of microprocessor 24. The current control circuit 58 is adapted to control current source 56 so that the latter generates a current of an amplitude determined by the microprocessor 24. The current control circuit 58 turns the current source 56 on or off for a pulse duration specified by the microprocessor. Finally, the charge control circuit 58 controls the charge circuit 50, again under the control of microprocessor 24. The current from source 56 flows through the cardiac impedance 48 and then returns.

The microprocessor sets the level of the charge voltage to be applied to the capacitor 52 by charge circuit 50 in accordance with the therapy selected by the microprocessor.

For example, for defibrillation pulses the circuit 50 charges the capacitor 52 to a very large amplitude. The charge required for cardioversion is of course much smaller. Thus, the same circuitry and same electrodes could be used to apply different types of therapies. Alternatively, different electrodes can be provided, in which case a switching network is used (not shown) to switch the current source 56 to different electrodes.

Figure 4:
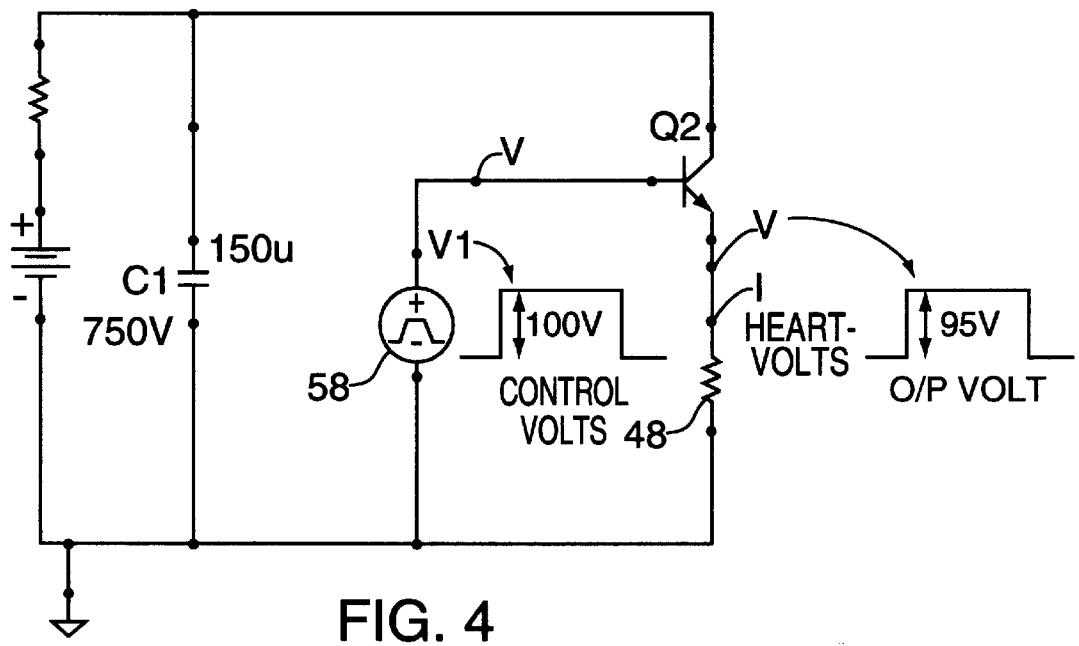
FIG. 4 shows a detailed circuit diagram of a first embodiment of the invention.

FIG. 4 shows an embodiment of current control circuit 58 wherein a constant voltage source is used. In this embodiment the current control circuit 58 generates a control signal V1. While V1 is low, transistor Q2 is off and the capacitor C1 is charged to about 750 Vdc. When V1 goes on, Q2 turns on and applies a constant voltage to the cardiac tissues (represented by resistor 48 having a value which has been previously determined). During this time, the capacitor Cl is slowly discharging; however, this has no effect on the voltage across 48.

In this configuration, a rectangular pulse, (as shown in FIG. 4) or any other type of pulse may be applied to the heart merely by shaping control signal V1 appropriately.

For example, if Q2 is an IGBT (Insulated Gate Bipolar Transistor) and for a value for 48 of 700 ohms, the control voltage V1 may be about 100 Vdc (peak value) to turn Q2 on. The resulting Vh applied to the heart may then be about 95 Vdc resulting in a constant current of about 1.4 amps.

Figure 5:
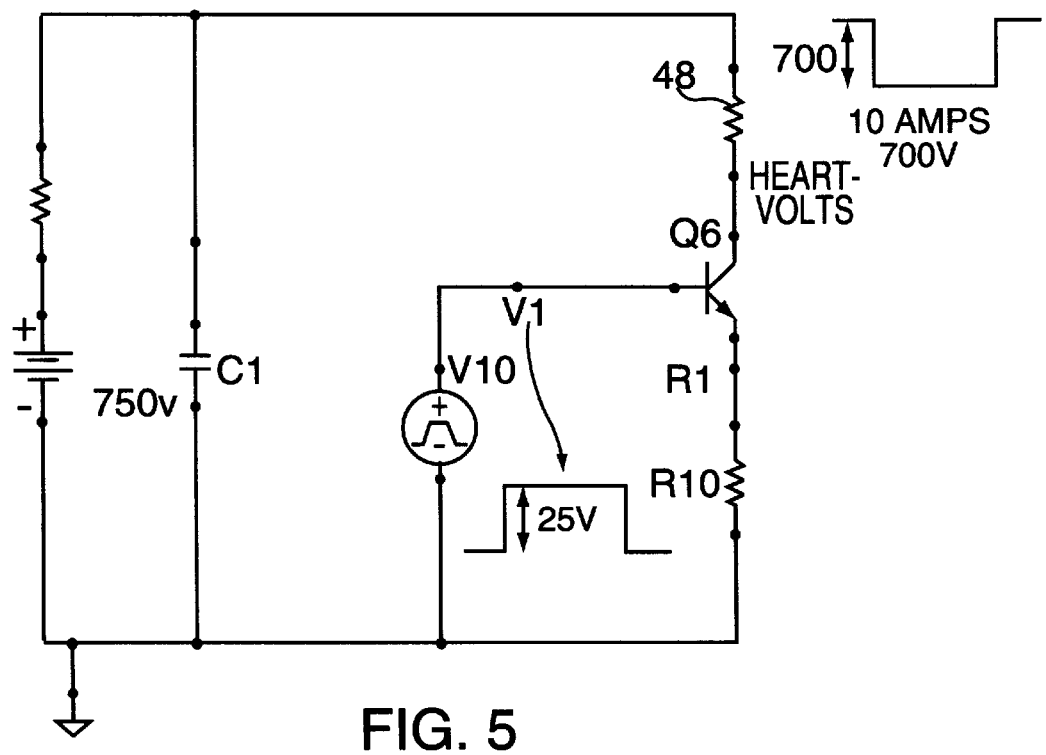
FIG. 5 shows a detailed circuit diagram of a second embodiment of the invention.

Referring now to FIG. 5, a constant current generator could be used as described herein. In this configuration, transistor Q6 is connected with its collector in series with heart tissue 48 and its emitter in series with a load resistor R10. In this configuration, the current control 58 generates a control signal V1. When signal V1 is off, transistor Q6 is off and capacitor C1 charges up to about 750 Vdc. When signal V1 goes high (to about 25V), transistor Q6 turns on and is biased so that the current I flowing through the heart is constant. For example, R10 could be about 2 ohms resulting in a current pulse through the heart of about 10 amps. In this configuration, the voltage across the heart tissue 48 is about 25 volts lower than the voltage across capacitor C1. Again, by shaping control signal V1, the defibrillation pulse applied to heart tissue 48 may be similarly shaped to any desired form.

In either case the current can be shaped to any desired waveform by an appropriate waveform applied to the base of the transistors Q2 or Q10.

Although reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable cardiac device for implementation into a patient's heart comprising:
   a controller that generates control signals defining any preselected waveform;
   a power supply;
   a controllable current source coupled to said power supply receiving said control signals; and
   an electrode extending to said heart:
   wherein said current source and said controller cooperate to provide through said electrode current pulses to the heart having any predetermined waveform.

2. The device of claim 1 wherein said power supply includes a battery and a capacitor, and wherein said current source is coupled to said capacitor.

3. The device of claim 1 further comprising a controller for controlling said controllable current source.

4. An implantable cardiac device for implantation into a patient, said device comprising;
   means for sensing intrinsic cardiac activity and generating sensed signals;
   means for receiving said sensing signals and for generating commands;
   an electrode extending to said heart;
   a current source; and
   control means receiving said commands and in response connecting selectively said electrode to said current source to apply therapeutic current pulses to said heart through said electrode;
   wherein said current source and said control means cooperate to provide through said electrode current pulses having any predetermined waveform.

5. The device of claim 4 further comprising a power supply providing power to said current source.

6. The device of claim 5 wherein said power source includes a battery, a capacitor and a charge control circuit for selectively charging said capacitor from said battery.

7. An implantable cardiac device comprising:
   a power source;
   a microprocessor that generates control signals defining therapeutic pulses having any predetermined arbitrary waveform profile;
   a controllable pulse generator connected to said microprocessor and said power source and being responsive to said control signals said controllable pulse generator and said microprocessor cooperating to generate said therapeutic pulses, said therapeutic pulses having the predetermined waveform profile defined by said control signals; and
   an electrode connected to said controllable current source to deliver said therapeutic pulses.

8. The device of claim 7 wherein said power source includes a capacitor having a capacitor voltage which decays during the generation of said therapeutic pulses, a switching transistor connected between said power source and said electrode and a control circuit coupled to said microprocessor and adapted to generate a control pulse coupled to said transistor for activating said transistor and thereby to generate said therapeutic pulse from said power source to said electrode, said therapeutic pulse being unaffected by the decay of said capacitor voltage.

9. The device of claim 8 wherein said power source comprises a battery and a capacitor, said capacitor being charged selectively to a predetermined peak voltage by said battery, said power source being connected to said transistor with said capacitor discharging through said transistor to generate said therapeutic pulse, and wherein said control circuit and said transistor cooperate to maintain said therapeutic pulse independently of a voltage of said capacitor.

10. The device of claim 9 wherein said transistor and said control circuit cooperate to generate a therapeutic voltage pulse through the heart and having said predetermined profile.

11. The device of claim 9 wherein said transistor and said current control circuit cooperate to generate a therapeutic current pulse through the heart and having said predetermined profile.

* * * * *